United States Patent
Alkon et al.

(10) Patent No.: US 6,821,979 B2
(45) Date of Patent: Nov. 23, 2004

(54) SYNERGISTIC ENHANCEMENT OF COGNITIVE ABILITY

(75) Inventors: Daniel L. Alkon, Bethesda, MD (US); Miao-Kun Sun, Gaithersburg, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 0 days.

(21) Appl. No.: 10/172,005

(22) Filed: Jun. 17, 2002

(65) Prior Publication Data

US 2003/0171385 A1 Sep. 11, 2003

Related U.S. Application Data

(60) Provisional application No. 60/362,081, filed on Mar. 7, 2002.

(51) Int. Cl.[7] .................... A61K 31/52; A61K 31/195
(52) U.S. Cl. .................... 514/263; 514/563; 514/567
(58) Field of Search .................... 514/263, 563, 514/567

(56) References Cited

U.S. PATENT DOCUMENTS 5,554,601 A * 9/1996 Simpkins et al. ............ 514/182
6,436,946 B1 * 8/2002 Mann ......................... 514/263

FOREIGN PATENT DOCUMENTS

WO   WO 00/56760    9/2000
WO   WO 00/62812   10/2000

OTHER PUBLICATIONS

Sun, Miao–Kun et al., "Carbonic Anhydrase Gating of Attention: Memory Therapy and Enhancement," *Trends in Pharmacological Sciences*, 23(2):83–89 (2002).
Alkon, Daniel L. et al., "Time Domains of Neuronal $Ca^{2+}$ Signaling and Associative Memory: Steps Through a Calexcitin, Ryanodine Receptor, $K^+$ Channel Cascade," *Trends in Neurosciences*, 1998.
Sun, Miao–Kun et al., "Pharmacological Protection of Synaptic Function, Spatial Learning, and Memory from Transient Hypoxia in Rats," *The Journal of Pharmacology and Experimental Therapeutics*, 300(2):408–416 (2002).
Sun, Miao–Kun et al., "Calexcitin Transformation of GABAergic Synapses: from Excitation Filter to Amplifier," *Proc. Nat. Acad. Sci. USA*, 96:7023–7028 (1999).
Sun, Miao–Kun, et al., "Functional Switching of GABAergic Synapses by Ryanodine Receptor Activation," *PNAS*, 97(22):12300–12305 (2000).
Seidl et al., "A taurine and caffeine–containing drink stimulates cognitive performance and will–being," Abstract, Amino Acids, vol. 19, No. 3–4, pp. 635–642, 2000.
International Search Report dated May 30, 2003 for Application No. PCT/US03/07102, filed Mar.7, 2003.
Gil, C.A. et al., "Study of the effects of treatment with theophylline on the cognitive process and behaviour of children with bronchial asthma," Allergol Immunopathol (Madr) 1993, Sep.–Oct. 21(5):204–6 (Abstract).
Fitzpatrick, M. F. et al., "Effect of therapeutic theophylline levels on the sleep quality and daytime cognitive performance of normal subjects," Arn. Rev. Respir. Dis. 1992, Jun., 145(6): 1355–8 (Abstract).
Mattila, M.J., "Caffeine and theophylline counteract diazeparn effects in man," Med. Biol. 1983;61(6):337–43 (Abstract).
Mohiuddin, A.A. et al., "Theophylline, aminophylline, caffeine and analogues for acute ischaemic stroke," Medscape from WebMD, The Cochrane Collaboration, 2002 (Abstract).
Weldon, D.P. et al., "Theophylline effects on cognition, behavior, and learning," Arch. Pediatr. Adolesc. Med. 1995 Jan.;149(1):90–3 (Abstract).
Newman, D. et al., "Physiological and neuropsychological effects of theophylline in chronic obstructive pulmonary disease," lsr. J. Med. Sci. 1994 Nov.;30(11):811–6.
Stein, M.A. et al., "Behavioral and cognitive effect of theophylline: a dose–response study," Ann Allergy 1993 Feb.;70(2):135–40 (Abstract).

* cited by examiner

*Primary Examiner*—Sreeni Padmanabhan
*Assistant Examiner*—Jennifer Kim
(74) *Attorney, Agent, or Firm*—Milbank, Tweed, Hadley & McCloy

(57) ABSTRACT

The present invention relates to the combination of a methylxanthine and a carbonic anhydrase activator to provide synergistic effects. The invention further relates to the improved/enhanced cognitive ability of individuals, particularly those suffering from various disorders, such as Alzheimer's Disease, stroke, hypoxia, general dementia, ADHD, mental retardation, and "sun down" syndrome.

2 Claims, 1 Drawing Sheet

SYNERGISTIC ENHANCEMENT OF COGNITIVE ABILITY

PRIORITY OF INVENTION

This application claims priority under 35 U.S.C. § 119(e) from U.S. Provisional Application No. 60/362,081 filed Mar. 7, 2002.

BACKGROUND OF THE INVENTION (i) Field of the Invention

The present invention relates to the cognitive enhancement through the administration of synergistic drugs.

(ii) Background of the Invention

Various disorders and diseases exist which affect cognition. Cognition can be generally described as including at least three different components: attention, learning, and memory. Each of these components and their respective levels affect the overall level of a subject's cognitive ability. For instance, while Alzheimer's Disease patients suffer from a loss of overall cognition and thus deterioration of each of these characteristics, it is the loss of memory that is most often associated with the disease. In other diseases patients suffer from cognitive impairment that is more predominately associated with different characteristics of cognition, for instance Attention Deficit Hyperactivity Disorder (ADHD), focuses on the individual's ability to maintain an attentive state. Other conditions include general dementias associated with other neurological diseases, aging, and treatment of conditions that can cause deleterious effects on mental capacity, such as cancer treatments, stroke/ischemia, and mental retardation. The present invention is directed toward the treatment of these and other similar disorders through the repair or amelioration of the cognitive deficits or impairments.

Cognition disorders create a variety of problems for today's society. Therefore, scientists have made efforts to develop cognitive enhancers or cognition activators. The cognition enhancers or activators that have been developed are generally classified to include nootropics, vasodilators, metabolic enhancers, psychostimulants, cholinergic agents, biogenic amines drugs, and neuropeptides. Vasodilators and metabolic enhancers (e.g. dihydroergotoxine) are mainly effective in the cognition disorders induced by cerebral vessel ligation-ischemia; however, they are ineffective in clinical use and with other types of cognition disorders. Of the developed cognition enhancers, typically only metabolic drugs are employed for clinical use, as others are still in the investigation stage. Of the nootropics for instance, piracetam activates the peripheral endocrine system, which is not appropriate for Alzheimer's Disease due to the high concentration of steroids produced in patients while tacrine, a cholinergic agent, has a variety of side effects including vomiting, diarrhea, and hepatotoxicity.

Ways to improve the cognitive abilities of diseased individuals have been the subject of various studies. Recently the cognitive state related to Alzheimer's Disease and different ways to improve patient's memory have been the subject of various approaches and strategies. In the case of Alzheimer's Disease, efforts to improve cognition, typically through the cholinergic pathways or though other brain transmitter pathways, have been investigated. This approach relies on the inhibition of acetyl cholinesterase enzymes through drug therapy. Acetyl cholinesterase is a major brain enzyme and manipulating its levels can result in various changes to other neurological functions and cause side effects. Cholinesterase inhibitors only produce some symptomatic improvement for a short time. Additionally, the use of cholinergic inhibitors only produces an improvement in a fraction of the Alzheimer's Disease patients with mid to moderate symptoms and is thus only a useful treatment for a small portion of the overall patient population. As a result, use of the cholinergic pathway for treatment of cognitive impairment, particularly in Alzheimer's Disease, has proven to be inadequate. Additionally, current treatments for cognitive improvement are limited to specific neurodegenerative diseases and have not proven effective in treatment across a broad range of cognitive conditions.

With regard to normal and abnormal memory both $K^+$ and $Ca^{2+}$ channels have been demonstrated to play key roles in memory storage and recall. For instance, potassium channels have been found to change during memory storage. (Etcheberrigaray, R., et al. (1992) Proceeding of the National Academy of Science 89:7184; Sanchez-Andres, J. V. and Alkon, D. L. (1991) Journal of Neurobiology 65:796; Collin, C., et al. (1988) Biophysics Journal 55:955; Alkon, D. L., et al. (1985) Behavioral and Neural Biology 44:278; Alkon, D. L. (1984) Science 226:1037). This observation, coupled with the almost universal symptom of memory loss in Alzheimer's patients, led to the investigation of ion channel function as a possible site of Alzheimer's Disease pathology, modulation by PKC, and its overall effect on cognition.

There still exists a need for the development of methods for the treatment for improved overall cognition, either through a specific characteristic of cognitive ability or general cognition. There also still exists a need for the development of methods for the improvement of cognitive enhancement whether or not it is related to a specific disease state or cognitive disorder. The methods and compositions of the present invention are needed and will greatly improve the clinical treatment for diminished cognitive ability whether related to a specific neurodegenerative disease, hypoxia, stroke or similar disorder. The methods and compositions also provide treatment and/or enhancement of the cognitive state.

SUMMARY OF THE INVENTION

The present invention relates to compounds, compositions, and methods for the treatment of conditions associated with the impairment of cognitive ability. In a preferred embodiment, the present invention further relates to compounds, compositions and methods for the treatment of conditions associated with neurodegenerative diseases, such as Alzheimer's Disease, memory dysfunction, and ischemia/stroke. Treatment provides for improved/enhanced cognitive ability. In another embodiment the present invention relates to compounds, compositions, and methods for the improvement/enhancement of cognitive ability.

In another aspect the present invention relates to the combination of a methylxanthine and carbonic anhydrase activators, to alter or test distinct molecular cascades, either in vivo or in vitro, in order to provide enhanced cognitive response. In a preferred embodiment the carbonic anhydrase activator is phenylalanine. In a preferred embodiment the methylxanthine is selected from theophylline and caffeine. Enhanced cognitive response, for example, can be employed in the treatment of Alzheimer's Disease.

Another aspect of the present invention relates to a method for treating conditions related to hypoxia and improving/enhancing the cognitive state of the subject comprising administering to the subject an effective amount of a composition combining a methylxanthine and a carbonic anhydrase activator. In a preferred embodiment the carbonic anhydrase activator is phenylalanine. In a preferred embodiment the methylxanthine is selected from theophylline and caffeine.

Another aspect of the present invention relates to a composition for improving/enhancing cognitive ability comprising: (i) an effective amount of a combination of a methylxanthine and a carbonic anhydrase activator; and (ii) a pharmaceutically effective carrier. In a preferred embodiment the carbonic anhydrase activator is phenylalanine. In a preferred embodiment the methylxanthine is selected from theophylline and caffeine. In a preferred embodiment the composition is used to improve/enhance cognitive ability associated with Alzheimer's Disease or stroke/ischemia. In another embodiment, the combination is delivered to subjects or models of Alzheimer's Disease or stroke/hypoxia.

In one embodiment of the invention the combination of a methylxanthine and a carbonic anhydrase activator results in improved cognitive abilities. In a preferred embodiment the carbonic anhydrase activator is phenylalanine. In a preferred embodiment the methylxanthine is selected from theophylline and caffeine. In one embodiment the improved cognitive ability is memory. In another embodiment the improved cognitive ability is learning. In another embodiment the improved cognitive ability is attention.

Another embodiment of the invention is a method of improving cognitive ability through the combination of a methylxanthine and a carbonic anhydrase activator. In another embodiment of the invention the combination of a methylxanthine and a carbonic anhydrase activator is delivered to "normal" subjects. In another embodiment of the invention the combination of theophylline and a carbonic anhydrase activator is delivered to subjects suffering from a disease, deteriorating cognitive faculties, or malfunctioning cognition. In a preferred embodiment the method is a method for treating Alzheimer's Disease cognitive degeneration. In a preferred embodiment the carbonic anhydrase activator is phenylalanine. In a preferred embodiment the methylxanthine is selected from theophylline and caffeine.

In a preferred embodiment of the invention the combination of a methylxanthine and a carbonic anhydrase activator is administered through oral and/or injectable forms including intravenously and intraventricularly. In another embodiment the combination may be administered through a sports drink or as a food supplement. In a preferred embodiment the carbonic anhydrase activator is phenylalanine. In a preferred embodiment the methylxanthine is selected from theophylline and caffeine.

The present invention therefore provides methods of treating impaired memory or a learning disorder in a subject, the method comprising administering thereto a therapeutically effective amount of a methylxanthine and a carbonic anhydrase activator. The compounds can thus be used in the therapeutic treatment of clinical conditions in which memory defects or impaired learning occur. In this way memory and learning can be improved and the condition of the subject can thereby be improved.

The present invention is also particularly suited to administration, particularly oral administration, since the combination of a methylxanthine (e.g. theophylline) and a carbonic anhydrase activator would be associated with a specific blood brain barrier transporter (BBB). In a preferred embodiment the transporter is the BBB transporter for phenylalanine.

The compositions and methods have utility in treating clinical conditions and disorders in which impaired memory or a learning disorder occurs, either as a central feature or as an associated symptom. Examples of such conditions which the present compounds can be used to treat include Alzheimer's Disease, multi-infarct dementia and the Lewy-body variant of Alzheimer's Disease with or without association with Parkinson's Disease; Creutzfeld-Jakob Disease, Korsakow's disorder, attention deficit hyperactivity disorder, hypoxia, ischeamic stroke, mental retardation, general dementia, and "sundown" syndrome.

The compositions and methods can also be used to treat impaired memory or learning which is age-associated, is consequent upon electro-convulsive therapy or which is the result of brain damage caused, for example, by stroke, an anesthetic accident, head trauma, hypoglycemia, carbon monoxide poisoning, lithium intoxication or a vitamin deficiency.

The pharmaceutical compositions and methods according to the invention are useful in the enhancement of cognition, prophylaxis and/or treatment of cognition disorders, wherein cognition disorders include, but are not limited to, disorders of learning acquisition, memory consolidation, and retrieval, as described herein.

DETAILED DESCRIPTION OF PREFERRED EMBODIMENTS

Figure 1:
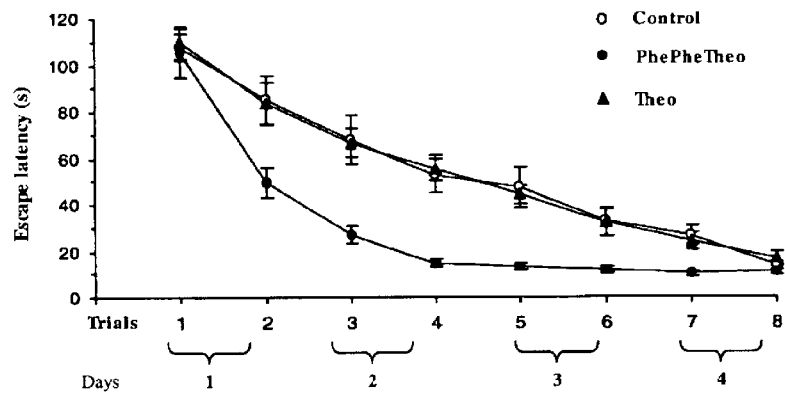
FIG. 1 illustrates the improved cognitive ability of treated rats using the Morris Water Maze paradigm as compared to control (phenylalanine) and theophylline alone treated rats. Phenylalanine-theophylline (orally; 50 mg/kg phenylalanine +2 mg/kg theophylline) or theophylline (2 mg/kg); 2 doses at 1 hr interval, with the 2nd dose administered about 0.5 hr prior to the 1st training trial of the day); 10 rats/group.

Memory loss and impaired learning ability are features of a range of clinical conditions. For instance, loss of memory is the most common symptom of dementia states including Alzheimer's Disease. Memory defects also occur with other kinds of dementia such as multi-infarct dementia (MID), a senile dementia caused by cerebrovascular deficiency, and the Lewy-body variant of Alzheimer's Disease with or without association with Parkinson's disease, or Creutzfeld-Jakob disease. Loss of memory is a common feature of brain-damaged patients. Brain damage may occur, for example, after a classical stroke or as a result of an anaesthetic accident, head trauma, hypoglycaemia, carbon monoxide poisoning, lithium intoxication, vitamin (B1, thiamine and B12) deficiency, or excessive alcohol use or Korsakow's disorder. Memory impairment may furthermore be age-associated; the ability to recall information such as names, places and words seems to decrease with increasing age. Transient memory loss may also occur in patients, suffering from a major depressive disorder, after electro-convulsive therapy (ECT). Alzheimer's Disease is in fact the most important clinical entity responsible for progressive dementia in ageing populations, whereas hypoxia/stroke is responsible for significant memory defects not related to neurological disorders.

Individuals with Alzheimer's Disease are characterized by progressive memory impairments, loss of language and visuospatial skills and behavior deficits (McKhann et al., 1986, Neurology, 34:939–944). The cognitive impairment of individuals with Alzheimer's Disease is the result of degeneration of neuronal cells located in the cerebral cortex, hippocampus, basal forebrain and other brain regions. Histologic analyses of Alzheimer's Disease brains obtained at autopsy demonstrated the presence of neurofibrillary tangles (NFT) in perikarya and axons of degenerating neurons, extracellular neuritic (senile) plaques, and amyloid plaques inside and around some blood vessels of affected brain regions. Neurofibrillary tangles are abnormal filamentous structures containing fibers (about 10 nm in diameter) that are paired in a helical fashion, therefore also called paired helical filaments. Neuritic plaques are located at degenerating nerve terminals (both axonal and dendritic), and contain a core compound of amyloid protein fibers. In summary, certain neuropathological features including intracellular neurofibrillary tangles, primarily composed of cytoskeletal proteins, and extracellular parenchymal and cerebrovascular amyloid, characterize Alzheimer's Disease. Further, there are now methods in the art for distinguishing between Alzheimer's patients, normal aged people, and people suffering from other neurodegenerative diseases, such as Parkinson's, Huntington's chorea, Wemicke-Korsakoff or schizophrenia further described for instance in U.S. Pat. Nos. 5,580,748 and 6,080,582.

Hypoxia/ischemic stroke remains one of the most devastating threats to humans and a challenge to neuropharmacologists. Because of the extreme sensitivity of neural structures involved in memory, especially the hippocampal CA1 pyramidal cells, to hypoxia and ischemia, memory impairment is common after cerebral hypoxia/ischemia, bypass surgery, or heart attack. Cognitive decline is evident in more than half to as many as three-quarters of patients at the time of discharge from hospitals after coronary-artery bypass grafting, as well as, in patients with chronic lung diseases or oropharyngeal abnormality. Hypoxic/ischemic consequences consist mainly of three forms: functional disruption, cellular injury, and delayed cell loss through apoptosis or necrosis, depending on the severity of the insult.

It is well established that functions of mammalian neurons are sensitive to acute hypoxia. The brain is a metabolically very active organ, but it contains virtually no $O_2$ reserve. Upon a sudden occlusion of brain circulation (ischemia), the brain is left with an $O_2$ content of about 0.2 ml/100 g and intracellular energy stores, which can support and maintain cellular energy for 1 to 2 min and 37° C. Cerbral hypoxia/ischemia, as occurs with environmental limitations, insufficient blood flow (cerebrovascular hemorrhage, brain tumor, vascular occlusion, or cardiac arrest, by pass surgery), respiratory dysfunction (obstruction of the airway, lung dysfunction, or neural control failure) or the use of some toxic substances, results in a high incidence of memory deficits and moderate-to-profound memory loss in humans. Irreversible damage to brain tissue is cause by 10 minutes of severe hypoxia in vivo and in vitro. However, episodes of transient hypoxia may be more relevant to a gradual memory decline. This may be particularly true following a brief hypoxic event or the continuous insult, which occurs with neurodegnerative diseases, such as AD, or during normal aging. Further, experiments demonstrate that induced hypoxic synaptic arrest compromises the ability of brains to learn and memorize.

Thus, a selective deficit in explicit memory functions is associated with neuronal loss/damage. While memory consolidation and processing is not limited to the hippocampus, the hippocampal CA1 pyramidal cells are among the most sensitive to hypoxic/ischemic damage. A major modulator of GABAergic inhibition in the hippocampus, present in CA1 pyramidal cells, is carbonic anhydrase. In humans and other species, including rats, the hippocampus has a broad role in information processing associated with memory, including spatial, declarative/relational, and episodic types of memory. In mammals, the hippocampus, a major component of the medical temporal lobe, mediates learning of associations between environmental contexts and sensory stimuli. Damage restricted to the hippocampus leads to deficits in cognitive tasks, particularly in spatial learning and memory. The existence of "place cells," pyramidal hippocampal neurons that fire when the animal is in a particular location in its environment, or when it receives a specific stimulus or performs a specific behavior in a particular place, provides additional support for the crucial role of the hippocampus in spatial cognition. Signal processing within the hippocampal network, including transmission of a θ rhythm from the septum to the hippocampus, is under strict control of interneurons that release GABA. Memory abnormalities that characterize the early stages of Alzheimer's Disease (AD) involve multiple neurotransmitter deficits in the hippocampal formation. It is known that alterations in synaptic spines and loss of dendrites during aging are associated with a significant decline in carbonic anhydrase in the brain and that this decline is even more dramatic in brains of AD patients.

Hypoxia significantly reduced cholinergic theta activity in rat CA1 field and intracellular theta in the CA1 pyramidal cells, recorded in hippocampal slices. Research suggests that hypoxia releases adenosine and produces an inhibition of synaptic transmission and intracellular signal cascade(s) involved in generation/maintenance of hippocampal CA1 theta activity. This is supported by studies indicating that the hypoxic synaptic arrest is prevented by blocking the adenosine A1 receptor and that spatial learning and functional impairment of the hippocampal CA1 synaptic plasticity are preventable by the adenosine A1 receptor antagonist, DPCPX. Additionally, it has been demonstrated that blocking adenosine A1 receptors prevent the impairment of spatial learning and memory and synaptic plasticity in response to non-injury hypoxic episodes.

Synapses are considered a critical site through which memory-related events realize their functional expression, whether the events involve changed gene expression and protein translation, altered kinase activities, or modified signaling cascades. Cognition and synaptic plasticity involve operational changes in preexisting synapses, the growth of new synapses, and processes that involve multiple synaptic transmitters and signaling molecules. A few proteins have been implicated in associative memory including $Ca^{2+}$ calmodulin II kinases, protein kinase C, calexcitin, a 22-kDa learning-associated $Ca^{2+}$ binding protein, and type II ryanodine receptors. Memories are thought to be a result of lasting synaptic modification in the brain structures related to information processing. $Ca^{2+}$ signaling, controlled by the endoplasmic reticulum (ER) and the plasma membrane, is a critical factor that induces changes in synaptic plasticity. Not only might neural activity control the amount of $Ca^{2+}$ stored in the ER, but $Ca^{2+}$ can also be released as a signal messenger to modify synaptic function, kinase activity, and protein synthesis.

Controlled $Ca^{2+}$ release from intracellular stores within a neuron represents an important mechanism for amplifying $Ca^{2+}$ signals received from outside the neuron. Such intracellular release is also important for the generation of stimulus-specific spatiotemporal patterning of cytosolic $Ca^{2+}$ signals, including $Ca^{2+}$ waves, and in switching responses to low-frequency stimulation from long-term depression to long-term synaptic potentiation. RyR enables the endoplasmic reticulum to play an amplifying role in $[Ca^{2+}]_i$ elevation in neurons.

Carbonic anhydrase activity, crucial for information coding and storage, is at least partially activated by intracellular release of $Ca^{2+}$ through the ryanodine receptors (RyR). For example, the RyR is involved in the GABA-mediated synaptic switch. The effect of $Ca^{2+}$ on carbonic anhydrase appears to be indirect. In human myelomonocytic cell lines, synthesis of carbonic anhydrase II is activated by protein kinase C, an effect that is blocked by 0.1 μm staurosporine. Hormones also regulate the activity of carbonic anhydrase via cAMP. Thus, the increase in carbonic anhydrase activity induced by adrenaline and dibutyryl-cAMP in erythrocytes is enhanced by theophylline, and phosphorylation by cAMP-dependent protein kinases activates carbonic anhydrase.

Carbonic anhydrase plays a crucial role in signal processing, long term synaptic transformation and attentional gating of memory storage. There are at least seven isozymes of carbonic anhydrase in humans. Carbonic anhydrase dysfunction impairs cognition and is associated with mental retardation, Alzheimer's Disease and aging. The pharmacological profile of carbonic anhydrase has been refined and specific activators have been developed. Carbonic anhydrase, a zinc-containing enzyme, catalyzes a reversible reaction between $CO_2$ hydration and $HCO_3^-$ dehydration. Recent studies indicate that activation of this enzyme provides a rapid and efficient mechanism to raise $HCO_3^-$ concentrations in memory-related neural structures. Increased $HCO_3$ flux through synaptic $GABA_A$ receptor channels alters postsynaptic neuronal responses to GABA and thus neuronal responses to diverse signal inputs. In this way, carbonic anhydrase functions as an effective attentional gate that controls signal transfer through the neural network. Alterations in carbonic anhydrase activity in hippocampal CA1 neurons provide a mechanism for switching between operational states at GABA releasing synapses, thereby gating signal transfer through the hippocampal network.

Because carbonic anhydrase is inactive without zinc at its active site, it is possible that zinc-containing proteins might function abnormally in dementia associated with AD and aging. Human carbonic anhydrase II has a high binding affinity for zinc. Even concentrations lower than 1 μm are sufficient to induce amyloid deposits, thus favoring redistribution of zinc from intra to extracellular sites. The zinc has been shown to induce immediate aggregation of an N-terminal fragment of β-amyloid ($Aβ_{1-40}$). $Zn^{2+}$ is concentrated to ~1 M in AD plaques and Aβ binds to zinc and to deposits at sites that contain high concentrations of zinc. The hippocampus contains the highest concentration of zinc in the brain and in AD there is a decrease in the intracellular concentration of zinc. The essential role of zinc in initiation of Aβ formation might explain why Aβ deposits are often concentrated in the hippocampus, rather than distributed uniformly throughout the brain. Reducing Aβ formation reduces behavioral impairment in AD transgenic mice whereas copper-zinc chelators solubilize Aβ and markedly reduce Aβ accumulation in AD transgenic mice. Furthermore, even if functional zinc deficiency does contribute to AD pathophysiology, carbonic anhydrase would not be the only protein affected.

Carbonic anhydrase inhibitors of the sulfonamide type (e.g., topiramate and acetazolamide) are widely used in the treatment of a variety of disorders such as glaucoma, epilepsy and gastro-duodenal ulcers. Carbonic anhydrase II deficiency syndrome in humans is also characterized by renal tubular acidosis, osteoperosis and mental retardation. Inhibition of carbonic anhydrase reduces and abolishes acetylcholine-mediated θ activity in the hippocampus. Thus, an important effect of carbonic anhydrase inhibition on hippocampal function is inhibition of θ activity, a synchronized hippocampal-activity rhythm that is required for spatial memory. In conscious animals, CNS administration of acetazolamide impairs spatial learning without affecting other sensory and/or locomotor behaviors. A single dose of acetazolamide, a specific inhibitor of carbonic anhydrase, reduces the magnitudes of θ-wave frequency activity measured by electroencephalogram during rapid-eye-movement sleep by 50% and acute inhibition of carbonic anhydrase impairs spatial memory.

Activators of carbonic anhydrase provided an important tool for the treatment of genetic carbonic anhydrase deficiencies and memory disorders. Many amines and amino acids (e.g., dopamine, noradrenaline, adrenaline, histamine, histidine, imidazoles, phenylalanine or derivatives thereof (See WO 00/56760) and 5-HT) are carbonic anhydrase activators. Activators of carbonic anhydrase facilitate the switch between excitatory and inhibitory effects of $GABA_A$ receptor stimulation that is induced by the temporal association between activation of cholinergic and GABAergic inputs. The combination of a methylxanthine (e.g. theophylline) and a carbonic anhydrase activator show cognitive enhancement of a specific molecular cascade, which in turn directly affects attention. The methylxanthine (e.g. theophylline) activates the ryanodine receptors of the endoplasmic reticulum. Additionally, the A-1 receptors are antagonized.

CNS administration of carbonic anhydrase activators (e.g., imidazole or phenylalanine) significantly enhances the ability of rats to learn a water-maze task and to recall the maze from memory. The present inventors have found that carbonic anhydrase activation is enhanced when combined with a methylxanthine, with theophylline being of particularly advantageous. Further discussion of carbonic anhydrase can be found in Carbonic anhydrase gating of attention: memory therapy and enhancement; Sun, Miao-Kun and Alkon, Daniel L., Trends in Pharmacological Sciences, Vol. 23 No. 2, pp. 83–89 (February 2002), which is hereby incorporated by reference in its entirety. These spatial-learning effects, which are mediated through attentional gating of relevant signals in the network, are sensitive to acetazolamide. Further, training rats in spatial water-maze task has been found to increase ryanodine receptor (RyR2) expression in the hippocampus.

The area of memory and learning impairment is rich in animal models, which are able to demonstrate different features of memory and learning processes. (See, for example, Hollister, L. E., 1990, Pharmacopsychiat., 23, (Suppl II) 33–36). The available animal models of memory loss and impaired learning involve measuring the ability of animals to remember a discrete event. These tests include the Morris Water Maze and the passive avoidance procedure. In the Morris Water Maze, animals are allowed to swim in a tank divided into four quadrants, only one of which has a safety platform beneath the water. The platform is removed and the animals are tested for how long they search the correct quadrant verse the incorrect quadrants. In the passive avoidance procedure the animal remembers the distinctive environment in which a mild electric shock is delivered and avoids it on a second occasion. A variant of the passive avoidance procedure makes use of a rodent's preference for dark enclosed environments over light open ones. Further discussion can be found in Crawley, J. N., 1981, Pharmacol. Biochem. Behav., 15, 695–699; Costall, B. et al, 1987, Neuropharmacol., 26, 195–200; Costall, B. et al, 1989, Pharmacol. Biochem. Behav., 32, 777–785; Barnes, J. M. et al, 1989, Br. J. Pharmacol., 98 (Suppl) 693P; Barnes, J. M. et al, 1990, Pharmacol. Biochem. Behav., 35, 955–962.

Further data suggest that the inducement of hypoxia and the damage that would normally result there from can be prevented through the administration of the combination of a methylxanthine (e.g. theophylline) and a carbonic anhydrase activator, indicating that the combination provides a neuroprotective effect. In a preferred embodiment the carbonic anhydrase activator is phenylalanine. As a result the present invention could also be used to treat a variety of conditions including but not limited to AD, general dementia, mental retardation, "sundown" syndrome, transient ischemia, and stroke.

Methylxanthines (i.e., theophylline) are often used to treat asthmatic conditions. Methylxanthines (i.e., theophylline) are also known to competitively inhibit phosphodiesterase, the enzyme that degrades cAMP. An increased concentration of cAMP is proposed to mediate the observed bronchodilation. Other proposed mechanisms of action include inhibition of the release of intracellular calcium and competitive antagonism of the bronchoconstrictor adenosine. The use of theophylline alone has provided a variety of studies regarding theophylline's effect on cognition and has generally been found to be insignificant. (See for example, Weldon, et al., Theophylline effects on cognition, behavior, and learning, Arch. Pediatr. Adolesc. Med., 149(1):90–3 (1995), Newman et al., Physiological and neuropsychological effects of theophylline in chronic obstructive pulmonary disease, Isr. J. Med. Sci., 30(11):811–6 (1994); Stein et al., Behavioral and cognitive effect of theophylline: a dose-response study, Ann. Allergy, 70(2):135–40 (1993); Gil et al., Study of the effects of treatment with theophylline on the cognitive process and behaviour of children with bronchial asthma, Allergol Immunopathol. 21(5):204–06 (1993); Fitzpatrick et al., Effect of therapeutic theophylline levels on the sleep quality and daytime cognitive performance or normal subjects, Am. Rev. Respir. Dis., 145(6):1355–58 (1992).

The use of the word, "normal" is meant to include individuals who have not been diagnosed with or currently display diminished or otherwise impaired cognitive function. The different cognitive abilities may be tested and evaluated through known means well established in the art, including but not limited to tests from basic motor-spatial skills to more complex memory recall testing. Non-limiting examples of tests used for cognitive ability for non-primates include the Morris Water Maze, Radial Maze, T Maze, Eye Blink Conditioning, Delayed Recall, and Cued Recall while for primate subjects test may include Eye Blink, Delayed Recall, Cued Recall, Face Recognition, Minimental, and ADAS-Cog. Many of these tests are typically used in the mental state assessment for patients suffering from AD. Similarly, the evaluation for animal models for similar purposes is well described in the literature.

The present compounds can be administered by a variety of routes and in a variety of dosage forms including those for oral, rectal, parenteral (such as subcutaneous, intramuscular and intravenous), epidural, intrathecal, intra-articular, topical and buccal administration. The dose range for adult human beings will depend on a number of factors including the age, weight and condition of the patient and the administration route.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening or emulsifying agents can be included.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration may be syrups, emulsions or suspensions. The syrups may contain as carrier, for example, saccharose or saccharose with glycerol and/or mannitol and/or sorbitol. In particular syrup for diabetic patients can contain as carriers only products, for example sorbitol, which do not metabolise to glucose or which metabolise only a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injection may contain, together with the active compound, a pharmaceutically acceptable carrier such as sterile water, olive oil, ethyl oleate, glycols such as propylene glycol and, if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compounds may be encapsulated within liposomes. The present compounds may also utilize other known active agent delivery systems.

The present compounds may also be administered in pure form unassociated with other additives, in which case a capsule, sachet or tablet is the preferred dosage form.

Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

In general, one of ordinary skill in the art, acting in reliance upon personal knowledge and the disclosure of this application, will be able to ascertain the amounts of these respective pharmaceutical agents and the amount of the compounds which should be administered to a subject to achieve the methods described herein. A "pharmaceutically effective amount," when referring to a combination of two or more agents, means an amount of each of the combined agents which is effective in eliciting the desired biological or medicinal response. For example, the pharmaceutically effective amount of a composition comprising a methylxanthine and a carbonic anhydrase inhibitor would be the amount of a methylxanthine and the amount of a carbonic anhydrase inhibitor that, when taken together, have a combined effect which is pharmaceutically effective. In accordance with the methods of treatment of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

It will be appreciated that the pharmacological activity of the compositions of the invention can be demonstrated using standard pharmacological models, which are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

All books, articles, or patents references herein are incorporated by reference to the extent not inconsistent with the present disclosure. The present invention will now be described by way of examples, which are meant to illustrate, but not limit, the scope of the invention.

EXAMPLES

Water-Maze

Figure 2A:
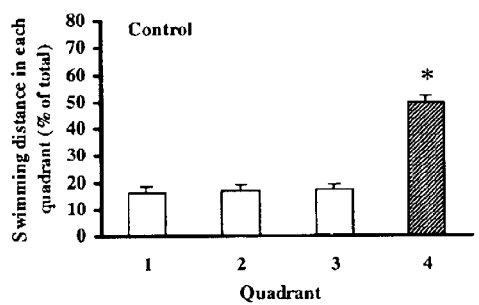
FIGS. 2(a) and 2(b) illustrate the swimming time, in each quadrant of the Morris Water Maze, for control rats and rats treated with PhePheTheo, respectively.
Figure 2B:
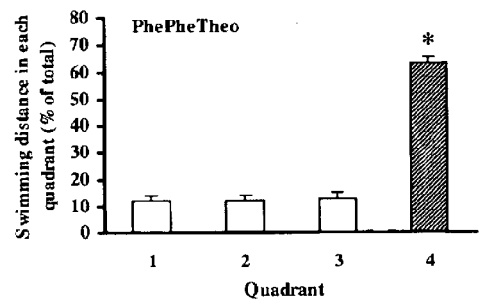
Figure 2C:
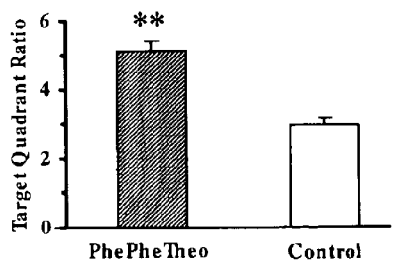
FIG. 2(c) demonstrates the cumulative target quadrant ratio for the Morris Water Maze.

The combination of a methylxanthine and a carbonic anhydrase activator was tested by administering phenylalanine (50 mg/kg) plus theophylline to rats 1.5 and 0.5 hours prior to subjecting the rats to the Morris Water Maze paradigm. Measuring the reduction of the escape latency in successive trials assessed cognitive ability, particularly learning. Memory and retention were assessed by measuring the time spent in the appropriate quadrant a day after the last trial. The rats treated with the combination of theophylline and a carbonic anhydrase activator, phenylalanine, exhibited both faster learning curves and enhanced retention compared to rats receiving phenylalanine alone or theophylline alone. (See FIG. 1 graph). Rats treated with the combination of theophylline and phenylalanine exhibited FIG. 2(*a*) and 2(*b*) illustrate the swimming time, in each quadrant of the Morris Water Maze, for control rats and rats treated with PhePheTheo, respectively. The amount of cumulative time spent in the target quadrant for treated rats compared to controls is for the Morris Water Maze shows a significant increase for treated rats. (See FIG. 2(*c*)). The results not only demonstrate that treated rats have improved learning, but that the rats also demonstrate improved recall.

What is claimed is:

1. A method for treating a subject with Alzheimer's Disease comprising administering to said subject a pharmaceutically effective amount of a composition comprising a single methylxanthine, at least one carbonic anhydrase activator, and a pharmaceutically acceptable carrier, wherein the methylxanthine is theophylline and the carbonic anhydrase activator is phenylalanine.

2. A method for treating a subject with Alzheimer's Disease comprising administering to said subject a pharmaceutically effective amount of a composition consisting of theophylline, phenylalanine and a pharmaceutically acceptable carrier.

* * * * *